United States Patent [19]

Frost

[11] 4,208,343

[45] Jun. 17, 1980

[54] 2,4 DIAMINO BENZONITRILE

[75] Inventor: Lawrence W. Frost, Murrysville, Pa.

[73] Assignee: Westinghouse Electric Corp., Pittsburgh, Pa.

[21] Appl. No.: 427,008

[22] Filed: Dec. 20, 1973

Related U.S. Application Data

[62] Division of Ser. No. 85,771, Oct. 30, 1970, Pat. No. 3,836,506.

[51] Int. Cl.$^2$ .................. C07C 121/52; C07C 121/78
[52] U.S. Cl. ........................ 260/465 E; 260/178; 260/326 N; 260/326 C; 260/465 R
[58] Field of Search .......... 260/47 CP, 78 TF, 326 C, 260/326 N, 465 E

[56] References Cited

U.S. PATENT DOCUMENTS 3,723,432   3/1973   Ott ................................. 260/281 Q

OTHER PUBLICATIONS

P. Vetesnik, J. Bielavsky, et al., Coll. Czech., Chem. Comm. 33, 2902 (1968).
P. Vetesnik, H. Hrebabecky, et al., Coll. Czech. Chem. Comm. 36, 2500 (1971).
M. F. G. Stevens, J. Chem. Soc. (London) (c), 1968, 348 (1968).

Primary Examiner—Mark L. Berch
Attorney, Agent, or Firm—Alex Mich, Jr.

[57] ABSTRACT

Deep curable polymers having heterocyclic ring systems such as isoindoloquinazolinedione ring systems prepared from novel cyanoimide polymers, most desirably 2'-cyanoimide polymers. Preferably the cyanoimide polymers are prepared from a diamine having at least one nitrile group in the two position to an amine group and a dianhydride having at least two cyclic anhydride groups. Copolymers may be prepared having other linkages, notably imide linkages, in addition to isoindoloquinazolinedione ring systems and/or other similar heterocyclic ring systems. The copolymers can be prepared by use of diamines containing one or more cyanoimide groupings and/or imide groups in their structure.

1 Claim, No Drawings

2,4 DIAMINO BENZONITRILE

The invention described herein was made in the performance of work under a NASA contract and is subject to the provisions of section 305 of the National Aeronautics and Space Act of 1958, Public Law 85-568 (72 Stat. 435; 42 U.S.C. 2457). sp This is a division of application Ser. No. 85,771 filed Oct. 30, 1970, now U.S. Pat. No. 3,836,506.

This invention relates to cyanoimide polymers and polymers having heterocyclic ring systems such as isoindoloquinazolinedione ring systems. It is particularly useful in providing polymers having isoindoloquinazolinedione ring systems and other similar heterocyclic ring systems which are curable in deep section from precursors having cyanoimide linkages.

Heterocyclic polymers having ring systems such as isoindoloquinazolinedione ring systems are generally known in the art. These polymers are characterized by their excellent thermal stability, excellent oxidative stability and toughness. Such polymers are particularly well suited for use as wire coatings, as films for electrical insulation and the like, as molding and laminating resins, and as varnish resins. However, utilization of these polymers has not been extensive because of their limited fabricating and processing characteristics. The polymers could not heretofore be made more than a few mils thick without the formation of voids, bubbles and cracks except by very slow curing.

A related problem is that isoindoloquinazolinedione polymers are generally infusible and insoluble in most solvents. Some of the polymers are capable of high temperature-pressure molding by a powder-sintering process and some are capable of being spun into fibers from strong acid solvents, but the application of such methods are extremely limited. The most useful method of fabricating has been to form the shaped article from solutions of precursors prior to forming polymers having the isoindoloquinazolinedione ring systems.

Shaped articles of polymers having isoindoloquinazolinedione ring systems have heretofore been made by first reacting an aromatic dianhydride with a bis-orthoaminoamide. The reaction product is a polyamide-acid which is soluble in selected solvents, such as N,N-dimethylformamide, N,N-dimethylacetamide or N-methylpyrrolidone, which may be removed from the product by evaporation or diffusion. Other solvents typical of this selected class are: N,N-diethylformamide, N,N-diethylacetamide, N,N-dimethylmethoxyacetamide, N-methylcaprolactam, dimethyl sulfoxide, tetramethyl urea, pyridine, dimethyl sulfone, hexamethylphosphoramide, tetramethylene sulfone, formamide, N-methylformamide, butyrolactone and N-acetyl-2-pyrrolidone. These solvents can also be used in combination with other solvents such as benzene, xylene, toluene, dioxane and cyclohexane, or used in admixture with each other. These solvents provide a solution polymerization medium for the synthesis of polyamide-acid and for forming the shaped article. The solute of polyamide-acid is then converted by use of heat and/or a convenient chemical dehydrating agent, such as acetic anhydride, to a polyimide amide.

The polyimide amide is thereafter cured by heating to cause cyclization to a polymer containing an isoindoloquinazolinedione ring system:

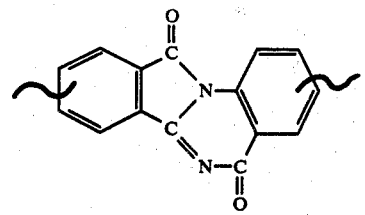

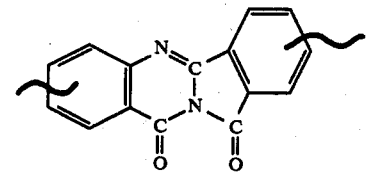

*While it has been generally recognized that general formula I represented the isoindoloquinazolinedione ring system, it has been suggested by Kurehara & Yoda, Synthesis of Ladder Polymers, 6 Polymer Letters 875–882 (1968), that the actual structure obtained is that shown by formula II.

*While it has been generally recognized that general formula I represented the isoindoloquinazolinedione ring system, it has been suggested by Kurehara & Yoda, Synthesis of Ladder Polymers, 6 Polymer Letters 875–882 (1968), that the actual structure obtained is that shown by formula II.

A general discussion of this method and some properties of isoindoloquinazolinedione polymers generally is set out in *Polymers Thermostables,* G. Rabilloud, B. Sillion and G. de Gaudemaris, 108 Die Makromolekulare Chemie. 18–51 (Nr. 2471) (1967).

A basic problem with this known method is that volatile by-products, such as water, are evolved during the final cure. The evolution causes bubbles, blisters and voids to form in the polymer and may cause hydrolysis of the polyimide amide with attendant reduction in the molecular weight of the polymer. A solution to this problem has been attempted by maintaining a very slow cure schedule on coatings of a few mils in thickness, but this has not proved to be a practical answer.

The present invention overcomes these disadvantages and difficulties. I provide deep curable polymers containing heterocyclic ring systems such as isoindoloquinazolinedione rings prepared from novel cyanoimide polymers. Stated another way, I provide a polymer containing isoindoloquinazolinedione ring systems and/or other similar heterocyclic ring systems made from precursor polymers containing cyanoimide linkages which can be formed in coatings of about 25 mils and thicker without substantial bubbles, blisters and voids.

Preferably the polymeric system containing the heterocyclic ring systems such as isoindoloquinazolinedione ring systems is made by first preparing a polymer containing 2'-cyanoimide linkages. By the application of heat, pressure or a catalyst, or a combination of these, at least some of the 2'-cyanoimide linkages are cyclicized to isoindoloquinazolinedione ring systems:

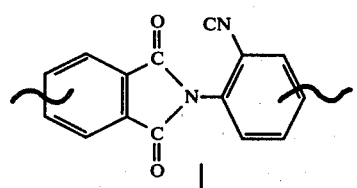

-continued

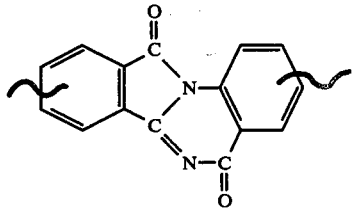

OR

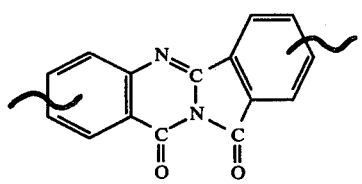

The cured polymer containing heterocyclic ring systems of the present invention can also be prepared from various other cyanoimide polymers. Illustrations of alternatives are as follows:

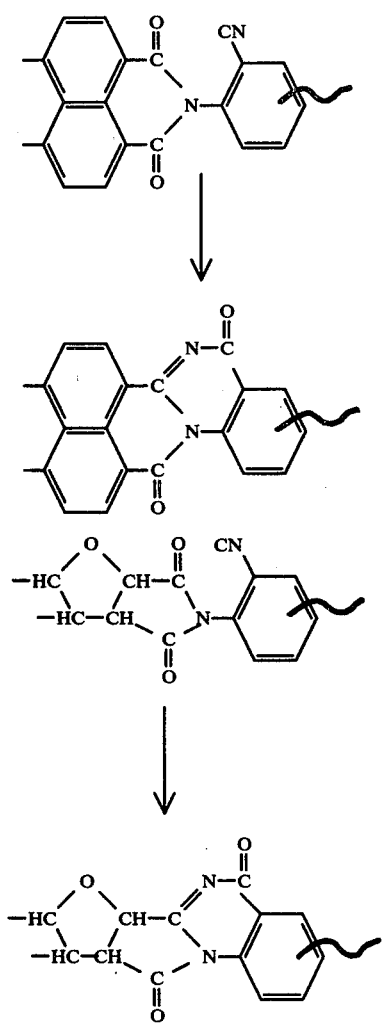

[A]

[B]

-continued

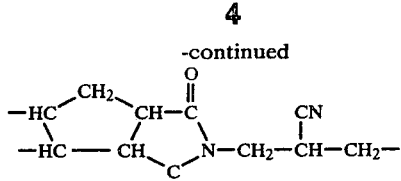

[C]

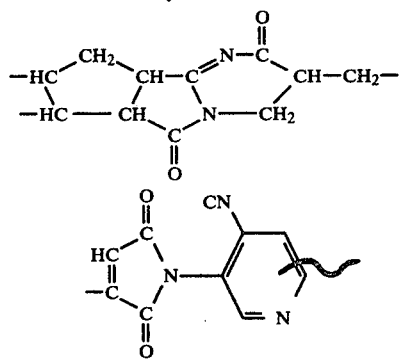

[D]

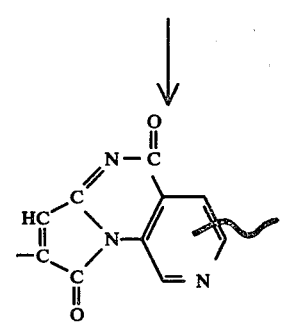

A common feature of these cyanoimide polymers is that they contain an imide ring of either five or six members and a nitrile group attached to a carbon atom in the two position of the group attached to the nitrogen atom of the imide ring.

For purposes of the present description, I use the term "isoindoloquinazolinedione ring systems" to broadly embrace isoindoloquinazolinedione ring systems and mutant isoindoloquinazolinedione ring systems. Strictly speaking, the isoindoloquinazolinedione ring system refers to an aromatic heterocyclic ring system having one five membered imide ring, two benzene rings, and another six membered ring as illustrated by (I) above, or the isomeric structure as illustrated by (II) above. Polymers containing this ring system can be obtained by cyclicizing polymers containing 2'-cyanoimide linkages as illustrated by (III) above. The present invention contemplates polymers having heterocyclic ring systems having six membered imide rings in place of the five membered imide rings, and/or aliphatic, cycloaliphatic, heterocyclic or different aromatic structures, or a combination of these structures, in place of one or both of the benzene rings. Examples of such mutant isoindoloquinazolinedione ring systems which may be prepared from cyanoimide precursors are illustrated by (A) through (D) above.

The nitrile-imide (or cyanoimide) polymers can be prepared in any suitable way. One method of preparation is by reacting a diamine, having at least one nitrile group in the two position (i.e. ortho or beta) to an amine group, with a dianhydride or its equivalent, preferably in substantially stoichiometric amounts. The initial reaction is preferably carried out in a selected solvent as set forth above. The reactants form a soluble cyano-amide-acid polymer. The cyano-amide-acid polymer is thereafter heated, preferably to about 150° C., to condense to a cyanoimide polymer.

The cyanoimide polymer is then cured by heating, preferably to between 300° C. and 400° C. for about 2 to 4 hours, to cause substantial cyclization to a polymer containing heterocyclic ring systems. Alternatively, the condensation and curing can be conducted concurrently. No volatile by-product is formed during the final cure. It is believed however that the presence of at least a trace amount of water is needed to effectuate the final cure and cause cyclization to the condensed heterocyclic ring systems.

The final curing temperatures and times can be greatly modified by the use of catalyst systems. For example, a combination of a peroxide such as hydrogen peroxide, benzoyl peroxide, tertiary-butyl perbenzoate, dicumyl peroxide, or methyl ethyl ketone peroxide, and a base such as sodium hydroxide, potassium hydroxide, sodium hydride, benzyltrimethylammonium hydroxide, sodium methoxide, or aluminum isopropoxide may be added as a catalyst system. A combination of hydrogen peroxide and potassium hydroxide has been found useful. Alternatively, acid catalysts such as boron trifluoride complexes and hydrogen chloride may be useful.

The diamine used in the present invention is preferably an ortho (or beta)-cyanodiamine. Examples of ortho (or beta)-cyanodiamines known or contemplated to be particularly suitable are: 2,4-diaminobenzonitrile, 2,5-diaminobenzonitrile, 3,3'-diamino-4,4'-dicyano-biphenyl, hydroquinone bis-(p-amino-m-cyanophenyl) ether, 3,3'-diamino-4,4'-dicyano diphenyl ether, 3,4-diaminoadiponitrile, 1,4-diamino-2,5-dicyanocyclohexane, 2,5-diamino-4-cyano-pyridine and 2,6-diamino-3,7-dicyanoacridine. Other specific cyano-diamines which may be used are N-(o-cyano-p-aminophenyl)-4-aminophthalimide and N,N-bis(p-amino-o-cyanophenyl)pyromellitic diimide.

Any dianhydride containing two cyclic anhydride groups is suitable for use in the present invention. Both five and six membered anhydride rings are useful. Dianhydrides known or contemplated to be particularly suitable are: 1,2,4,5-benzenetetracarboxylic dianhydride (PMDA), 3,4,3',4'-benzophenonetetracarboxylic dianhydride (BTDA), 2,3,6,7-naphthalene tetracarboxylic dianhydride, 1,2,5,6-naphthalene tetracarboxylic dianhydride, 1,8,4,5-naphthalene tetracarboxylic dianhydride, 3,4,3',4'-biphenyl tetracarboxylic dianhydride, 2,3,2',3'-biphenyl tetracarboxylic dianhydride, bis-(3,4-dicarboxyphenyl)methane dianhydride, 2,2-bis-(3,4-dicarboxyphenyl)propanedianhydride, 1,2,3,4-cyclopentane tetracarboxylic dianhydride, tetrahydrofurane-2,3,4,5-tetracarboxylic dianhydride, 1,2,5,6-hexane tetracarboxylic dianhydride, bis-(3,4-dicarboxyphenyl)sulfone dianhydride, bis-(3,4-dicarboxyphenyl)ether dianhydride, and mellophanic dianhydride. Other equivalent compounds may be substituted in whole or in part for the dianhydrides. Especially useful compounds of this class are those containing two ortho-chlorocarbonyl ester groupings, or one such grouping and one anhydride group. Examples are: 2,5-bis(carbomethoxy) terephthaloyl chloride, 4,6-bis(carbobutoxy)isophthaloyl chloride, 4,4'-bis(carboethoxy)-3,3'-benzophenonedicarbonyl chloride, 1,8,4,5 naphthalene tetracarboxylic-1,8-anhydride-dimethyl ester-5-acid chloride. Other halogens can be substituted for the chlorine in these compounds.

Illustrative of the reaction mechanism involved in one aspect of the invention in a non-polymeric system is the reaction mechanism in the synthesis of isoindolo [2,1-a]quinazoline-5,11-dione:

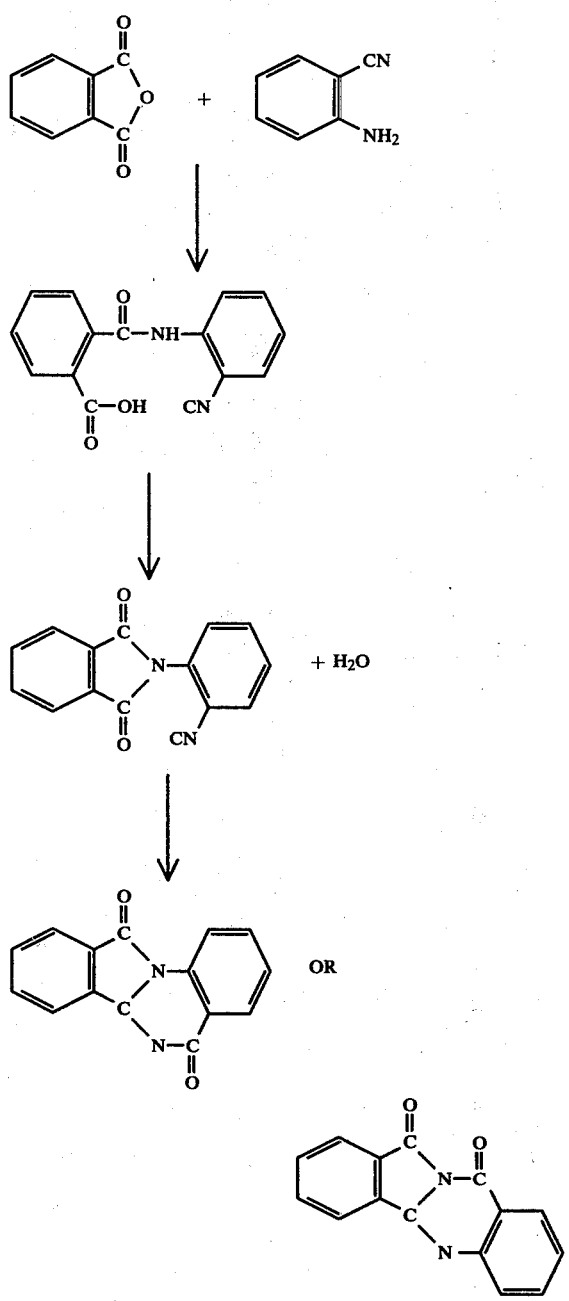

A solution of sublimed phthalic anhydride in ethyl acetate is reacted with a solution of anthranilonitrile in ethyl acetate to form 2'-cyanophthalanilic acid. The 2'-cyanophthalanilic acid is then boiled with acetic anhydride to convert the acid to 2'-cyanophthalanil. The 2'-cyanophthalanil is thereafter boiled in a mixture containing 2% potassium hydroxide and 2.4% hydrogen peroxide, cooled and neutralized with hydrochloric acid to cyclicize it and form isoindolo [2,1-a]quinazoline-5,11-dione. A similar procedure is set forth by Bogert and Hand, 24 J. Am. Chem. Soc., 1031 (1902) for preparing 2-methyl-4-ketodihydroquinazoline from N-acetylanthranilonitrile.

Various linkages other than isoindoloquinazolinedione and similar heterocyclic ring systems can be incorporated into the polymer chains. This can be accomplished by mixing other difunctional and/or polyfunctional compounds containing the desired linkage or a precursor thereof into the polyamide-acid solution, or by using a diamine and/or dianhydride containing the desired linkage. Various suitable vinyl compounds, polyols, polyacids, polyamines, polyesters, polyurethanes, epoxides and the like will occur to those skilled in the art. Similarly, other polymeric systems can be admixed with the cyanoimide polymers by incorporation into the polyamide-acid solution.

Copolymers that are particularly desirable are those containing both isoindoloquinazolinedione ring systems and imide linkages. For example a polymer containing the following repeating unit can be prepared from 2,4-diaminobenzonitrile and 1,2,4,5-benzenetetracarboxylic dianhydride:

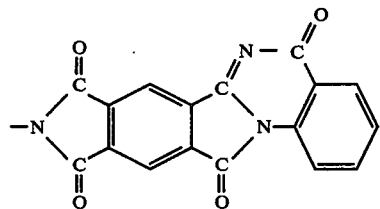

Similarly, polymers containing both isoindoloquinzaolinedione rings and imide linkages can be prepared by use of diamines containing one or more cyano-imide groupings in their structure. Examples are: 4-amino-N-(2-cyano-4'-aminophenyl)phthalimide; N,N'-(2-cyano-4-aminophenyl)pyromellitimide; N,N'-(2-cyano-4-aminophenyl)-3,3',4,4'-benzophenonetetracarboxylic diimide; and 4,4'-dicyano-3,3'-bis(4-aminophthalimido)-biphenyl. Alternatively, precursor amide-acid groups can be substituted in each case for the corresponding imide. In the first example this would be 4(or 5), 4'-diamino-2-carboxy-2'-cyanobenzanilide. An advantage of this method of preparation is that the imino groups are not deactivated by ortho nitrile groups. Consequently, high molecular weight resins are readily obtained by condensation with a dianhydride or an equivalent.

Polymers of several types can be made from the cyanoimide diamines and dianhydrides. In each case one or more cyano-imide groupings are present and can be cured to cause cyclization to the isoindoloquinazolinedione ring systems. In addition to the imide-cyano groupings and imide linkages other linkages or combinations can be produced. For example, it is contemplated that the cyanoimide diamine can be reacted with:

(a) an aromatic dianhydride, such as PMDA, or a diester diacyl chloride, such as 2,5-bis-(methoxycarbonyl)terephthaloyl chloride, to form additional imide linkages.

(b) a diacyl chloride such as isophthaloyl chloride or a diester such as diethyl or diphenyl terephthalate to form amide linkages.

(c) a compound containing one isolated carboxylic function and one adjacent pair of carboxylic functions such as trimellitoyl anhydride chloride, trimellitic anhydride, 2-(methoxycarbonyl) terephthaloyl chloride, or 4-(ethoxycarbonyl)isophthaloyl chloride to form amide and imide linkages.

(d) di-isocyanate such as 4,4' diphenyl methane diisocyanate to form urea linkages.

Accordingly the present invention provides a route to the obtention of deep section cured polymers having isoindoloquinazolinedione ring systems and/or similar heterocyclic ring systems in combination with other linkages and/or polymeric systems. Such ring systems provide excellent thermal as well as oxidative stability as well as adding tremendous chain stiffening.

Other details, objects and advantages of my invention will be apparent from the following nonlimiting examples.

Examples I to VI are addressed to the preparation of diaminonitriles which are known or contemplated to be particularly useful. Examples VII-XII are addressed to the preparation of the polymers from a dianhydride or the like and a diaminonitrile known or contemplated to be particularly useful.

EXAMPLE I: Preparation of 2,4-Diaminobenzonitrile.

2,4-diaminobenzonitrile was prepared as follows:

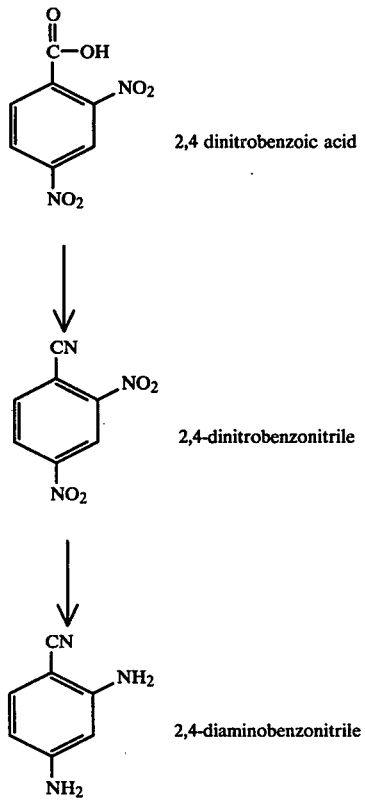

2,4-dinitrobenzonitrile was prepared from 2,4-dinitrobenzoic acid and benzenesulfonamide by the method of Oxley, Partridge, Robson and Short, J. Chem. Soc., 1946, 763. The product was purified by chromatography on alumina, using tetrahydrofuran as a solvent: yield, 56%; m.p. 102° C.

A solution of 74.6 g. of stannous chloride dihydrate, 75 ml. concentrated HCl, and 150 ml. ethanol was cooled in an ice bath and stirred while adding 9.66 g. (0.05 mole) of powdered 2,4-dinitrobenzonitrile at a rate that maintained a temperature of 25°–30° C. The resulting yellow solution was held at 40° C. for 90 minutes while a stream of nitrogen was blown over the surface to evaporate most of the ethanol. The residue was a yellow slurry, which was cooled in an ice bath and stirred while a solution of 70 g. NaOH in 280 g. of water was added slowly. The mixture was then filtered. The filtrate was extracted four times with ethyl acetate and the extract evaporated to dryness. The residue was combined with the solids from the filtration, and the mixture was extracted with four 150 ml. portions of boiling benzene. The benzene solution was evaporated to dryness to give 4.75 g. of crude product, which was recrystallized from benzene to give 4.67 g. (70% yield) of pure 2,4-diaminobenzonitrile, m.p. 105° C. Anal. Calculated for $C_7H_7N_3$: C, 63.19; H, 5.30; N, 31.56. Found: C, 62.54, 62.67; H, 5.24, 5.09; N, 31.32, 31.10.

EXAMPLE II: Preparation of 3,3'-Diamino-4,4' dicyanobiphenyl.

3,3'-diamino-4,4'-dicyanobiphenyl was prepared as follows:

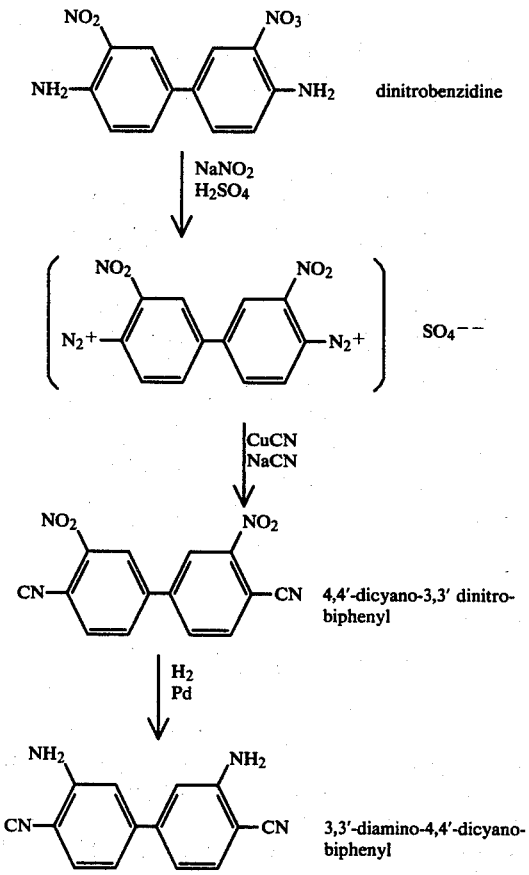

سodium nitrite (3.0 g., 0.0435 mole) was added slowly to 30 ml. of concentrated sulfuric acid, with stirring. The resulting solution was cooled to 25° C., and stirred while 5.48 g. (0.020 mole) of 3,3'-dinitrobenzidine was added slowly, with cooling to maintain a temperature of 20°–25° C. After an hour of stirring a viscous brown solution was obtained, to which was slowly added 30 ml. of glacial acetic acid, using an ice bath to keep the temperature at 25°–30° C. The resulting solution was poured onto 200 g. of crushed ice and a solution of 32 g. (0.8 mole) of sodium hydroxide in 50 ml. of water was added slowly with cooling (30° C.). The resulting solution was added slowly to a stirred solution of 5.9 g. (0.12 mole) of sodium cyanide, 4.48 g. (0.05 mole) of cuprous cyanide, 32 g. (0.8 mole) of sodium hydroxide and 160 ml. of water. A mildly exothermic reaction occurred, with liberation of nitrogen and a final temperature of 38° C. The mixture was stirred at 40°–60° C. for 30 minutes, let stand overnight at room temperature, and filtered. The solid product was washed with water and dried at 110° C. under vacuum to give 4.6 g. of black powder.

A 1.00 g. sample of the black powder was extracted with three 20 ml. portions of boiling xylene. The extracts yielded 0.36 g. of yellow powder, which was further purified by column chromatography. In a typical run a 0.20 g. sample of the yellow powder was dissolved in 15 ml. of tetrahydrofuran and applied to a column of neutral alumina. Additional tetrahydrofuran was used to elute the column. A 20 ml. middle fraction was evaporated to dryness to give 0.18 g. of 3,3'-dinitro-4,4'-dicyanobiphenyl as a yellow powder, m.p. 246° C. Anal. Calculated for $C_{14}H_6N_4O_4$: C, 57.15; H, 2.06; N, 19.04; O, 21.75. Found: C, 57.20, 57.35; H, 2.37, 2.36; N, 17.83, 17.92; O, 22.77, 22.59. The infrared spectrum had str absorption bands at 2230 (nitrile), 1531 (nitro) and 1 (nitro) cm$^{-1}$.

The 3,3'-diamino-4,4'-dicyanobiphenyl was prepared by dissolving 4,4'-dicyano-3,3'-dinitrobiphenyl (1.14 g., 0.0039 mole) in 200 ml. of tetrahydrofuran and hydrogenating in a Parr shaker at 55 psi and 70° C. for one hour, using 0.5 g. of 5% Pd-on-C catalyst. The catalyst was filtered off, and the filtrate was evaporated to dryness to give 1.07 g. of yellow powder. A 0.20 sample of the product was dissolved in 10 ml. of tetrahydrofuran and applied to a column of neutral alumina. The column was eluted with absolute ethanol to give a fraction which was evaporated to dryness and baked at 75° C. in vacuum to give 0.08 g. of 3,3'-diamino-4,4'-dicyanobiphenyl as a yellow powder, m.p. 243° C. Anal. Calculated for $C_{14}H_{10}N_4$: C, 71.78; H, 4.31; N, 23.92. Found: C, 71.65, 71.48; H, 4.28, 4.38; N, 22.65, 22.60.

EXAMPLE III: Preparation of 3,3'-Diamino-4,4'-Dicyanodiphenyl Ether.

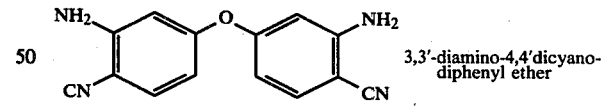

3,3'-diamino-4,4'dicyano-diphenyl ether

One hundred fifty ml. of concentrated sulfuric acid was stirred while 15 g. (0.22 mole) of sodium nitrite was added slowly. The mixture was then heated to 70° C. for a few minutes until clear. The solution was cooled and held at 20°–30° C. while adding 29 g. (0.1 mole) of 3,3'-dinitro-4,4'-oxydianiline. The resulting dark solution was stirred for one hour, after which 150 ml. of glacial acetic acid was added slowly, with stirring and cooling to keep the temperature at 25°–30° C. The resulting solution was poured onto 1000 g. of crushed ice, with stirring. A solution of 160 g. of sodium hydroxide in 250 ml. of water was added with stirring. Ice was added as needed to keep the temperature below 30° C. The resulting clear brown solution was added with stirring to the following solution:

| | |
|---|---|
| sodium cyanide | 29.5 g. (0.6 mole) |
| cuprous cyanide | 22.4 g. (0.25 mole) |
| sodium hydroxide | 160 g. (4 moles) |
| water | 800 ml., | cooling as necessary to keep the temperature below 50° C. After the addition the mixture was held at 50°-60° C. for 0.5 hour and allowed to stand overnight at room temperature. It was filtered, and the solid material washed with water and dried at 100° C. in vacuum to give 41 g. of dark red powder.

Three similar batches were combined and extracted four times with 2700 ml. portions of boiling xylene. The combined extract was evaporated to dryness in a stream of nitrogen to give 29.5 g. of solids. This material was dissolved in 1600 ml. of warm tetrahydrofuran. The solution was poured through a column of adsorption alumina, which was eluted with additional tetrahydrofuran. Successive fractions were collected and evaporated to dryness separately in a stream of nitrogen. Residues with similar melting points were combined to give 18.9 g. of 3,3'-dinitro-4,4'-dicyanodiphenyl ether, m.p. 202°-204° C., which was dissolved in 189 ml. of N,N-dimethylacetamide, and 0.1 g. of 10% Pd-on-C catalyst was added. The mixture was hydrogenated in a Parr shaker at 90° C. and 50 psi. The catalyst was filtered off and the filtrate poured into excess water. After standing several days in a refrigerator, the mixture was filtered. The solid product was washed with water and dried at 100° C. in a vacuum to give 6.48 g. of 3,3'-diamino-4,4'-dicyanodiphenyl ether, m.p. 156° C.

EXAMPLE IV: Preparation of Hydroquinone bis(4-amino-3-cyanophenyl) ether.

Hydroquinone bis(4-amino-3-cyanophenyl) ether was prepared as follows:

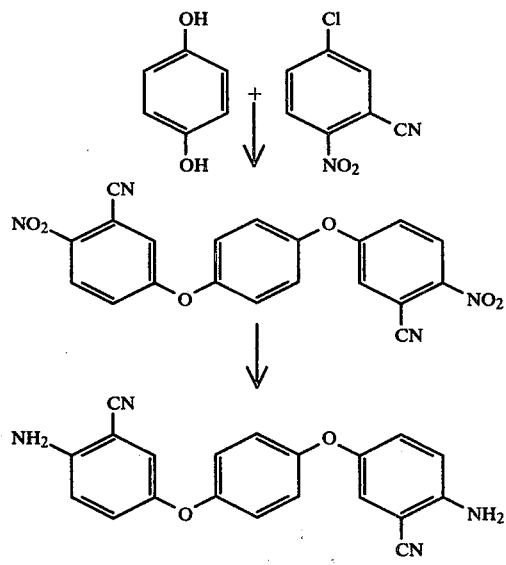

A solution of 5.51 g. (0.05 mole) of 1,4 benzenediol in 100 ml. of water was stirred under nitrogen while a solution of 6.47 g. (0.10 mole) of potassium hydroxide (86.5%) in 20 ml. of water was added, followed by 200 ml. of toluene. The mixture was refluxed with stirring, using a Dean-Stark trap, until the water was largely removed. Dimethylacetamide (200 ml.) was then added, and solvent was distilled off until the pot temperature reached 150° C. The mixture was cooled to 50° C., and a solution of 18.26 g. (0.10 mole) of 5-chloro-2-nitrobenzonitrile (Aldrich Chemical Co.) in 50 ml. of dimethylacetamide was added with stirring. The mixture was stirred for 90 minutes at room temperature, 2 hrs. at 125° C., and 1 hr. at 155° C. After cooling to room temperature it was filtered. The filtrate was evaporated to dryness and the residue washed with 250 ml. of tetrahydrofuran. The residual solid was dried in vacuum at 100° C. to give 11.64 g. (58% yield) of hydroquinone bis(4-nitro-3-cyanophenyl) ether, m.p. 233° C. Anal: Calculated for $C_{20}H_{10}N_4O_6$: C, 59.71; H, 2.51; N, 13.92; O, 23.86. Found: C, 59.27, 59.42; H, 2.85, 2.75; N, 13.81, 13.60; O, 24.18, 23.92. An additional 1.48 g. (7.4% yield) of product was recovered from the tetrahydrofuran washings.

Reduction of this compound to hydroquinone bis-(4-amino-3-cyanophenyl) ether can be accomplished with stannous chloride, using a procedure similar to that of Example 1.

EXAMPLE V: Preparation of N-(2'-cyano-4'-amino phenyl)-4-aminophthalimide.

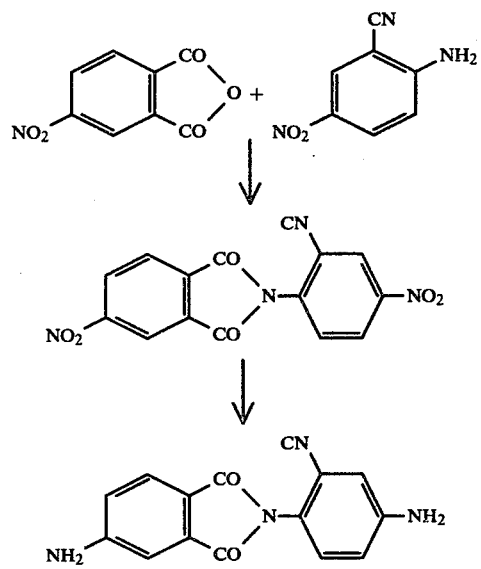

Equimolar quantities of 4-nitrophthalic anhydride and 5-nitroanthranilonitrile (Aldrich Chemical Co.) can be heated in a solvent such as dimethylformamide, dimethylacetamide or dimethyl sulfoxide to give N-(2'-cyano-4'-nitrophenyl)-4-nitrophthalimide, which can be isolated and purified by recrystallization. An alternative method of synthesis for this intermediate is the reaction of 2-chloro-5-nitrobenzonitrile with the potassium salt of 4-nitrophthalimide, using one of the solvents listed above.

Reduction of N-(2'-cyano-4'-nitrophenyl)-4-nitrophthalimide to N-(2'-cyano-4'-aminophenyl)-4-aminophthalimide can be done with stannous chloride, using a procedure similar to that of Example 1, or by catalytic hydrogenation over a palladium, platinum, or nickel catalyst.

EXAMPLE VI: Preparation of N,N',-bis(4-amino-2-cyanophenyl) diimides.

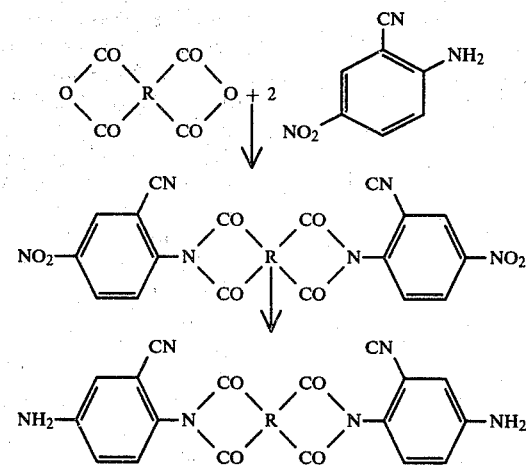

R in the above equation represents a tetravalent organic radical in which the free bonds are arranged in two pairs of adjacent bonds. Examples are 1,2,4,5-or 1,2,3,4-tetrasubstituted benzene; 1,2,3,4-tetrasubstituted cyclopentane; 2,3,4,5-tetrasubstituted tetrahydrofurane; or 3,3', 4,4'-tetrasubstituted benzophenone.

The synthesis of these compounds is carried out by essentially the same procedure as Example IV, using two moles of 5-nitroanthranilonitrile and one mole of a dianhydride. Suitable dianhydrides are listed in column 6 of U.S. Pat. No. 3,179,632.

EXAMPLE VII: Preparation of Polymer from BTDA and 3,3'-diamino-4,4'-dicyanodiphenyl Ether.

0.50 g. (0.002 mole) of the product of Example III dissolved in 3.45 g. of N,N-dimethylacetamide (DMAC) was stirred while adding 0.65 g. (0.002 mole) of 3,4,3',4'-benzophenonetetracarboxylic dianhydride. The mixture was warmed slightly to give a clear solution. One gram samples of the solution were placed in three aluminum dishes, 2" in diameter. The first was baked for 3 hrs. at 150° C. to give a clear amber film of polymer largely in the imide form. An additional one hour at 300° C. completed conversion to the imide and gave a hard resin. The second sample received the same cure plus 2 hours at 350° C. The third sample was cured the same as the second with an additional 2 hrs. at 400° C. Sample two was partially converted to polymer containing isoindoloquinazolinedione rings, and in sample three the conversion was essentially complete to polymer containing isoindoloquinazolinedione rings, as shown by infrared spectroscopy.

EXAMPLE VIII: Preparation of Polymer from 2,4-diaminobenzonitrile and 2,5-dicarbomethoxyterephthaloyl chloride.

A solution of 1.3316 g. (0.01 mole) of 2,4-diaminobenzonitrile prepared in accordance with Example 1 in 15 ml. of dimethylacetamide was stirred while 3.1910 g. (0.01 mole) of 2,5-dicarbomethoxyterephthaloyl chloride was added slowly. An exothermic reaction occurred with the formation of a viscous yellow solution containing a fine white precipitate. This solution was allowed to stand at room temperature for 2 hours and was then poured into rapidly stirred water. A white precipitate formed, was filtered off, washed with water, and dried at 70° C. in vacuum to give 3.59 g. (95% yield) of polymer as a white powder. The inherent viscosity of this polymer (0.5% solution in DMAC, 25° C.) was 0.20 dl/g. The product at this point was largely in the polyamide-ester form:

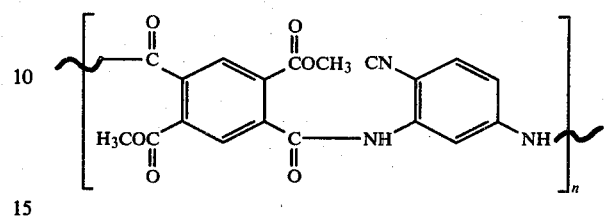

A film was cast from a 25% solution of the white powder in dimethylacetamide by spreading in an aluminum dish and baking for an hour at 150° C. and two hours at 200° C. A clear yellow film was obtained of polymer which was largely in a cyano-imide form:

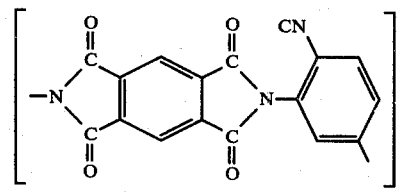

Further heating at 350° C. and 400° C. gave a brown film of polymer containing isoindoloquinazolinedione ring systems and imide linkages:

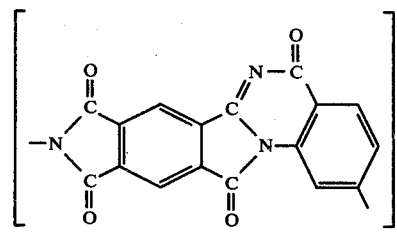

EXAMPLE IX: Preparation of Polymer from BTDA and 2,4-Diaminobenzonitrile.

A mixture of 1.3316 g. (0.01 mole) of 2,4-diaminobenzonitrile (Ex. 1), 3.222 g. (0.01 mole) of 3,4,3'4'-benzophenonetetracarboxylic dianhydride, and 15 ml. of N,N-dimethylacetamide was stirred at 40° C. for a few minutes to give a clear amber solution. This solution was held at 100° C. for two hours and was then boiled gently for 90 minutes to give a clear amber solution of very high viscosity. Dilution to 35% solids gave a clear solution of polymer which was partly in the amide-acid form and partly in the imide-nitrile form. Viscosity was Gardner T-U. A thin film of the solution in an aluminum dish was baked for 3 hours at 160° C. and 2.5 hours at 200° C. to give a clear yellow continuous solid film of imidenitrile polymer. Additional baking at 250° C. and at 400° C. gave further cyclization and the formation of isoindoloquinazolinedione ring systems.

EXAMPLE X: Preparation of Polymer from PMDA.

The procedure of Example VII is repeated, using 0.436 g. (0.002 mole) of pyromellitic dianhydride in place of the 3,4,3'4'-benzophenonetetracarboxylic dianhydride. In place of the product from Example III is substituted 0.684 g. (0.002 mole) of the product of Example IV, or 0.468 g. (0.002 mole) of the product of Example II. In each case an imide-nitrile polymer is produced, which cures on further heating to a polymer containing isoindoloquinazolinedione ring systems.

EXAMPLE XI: Preparation of Polymer from Imide-Nitrile Diamines and Dianhydrides.

A solution of 2.78 g. (0.01 mole) of the product of Example V in 50 ml. of N,N-dimethylacetamide is stirred while 3.22 g. (0.01 mole) of 3,4,3',4'-benzophenonetetracarboxylic dianhydride is added slowly. A solution of polymer is obtained which can be cured by heat to an imide-nitrile polymer. Further heating causes further cyclization to a polymer containing both imide linkages and isoindoloquinazolinedione ring systems.

Similar results are obtained in the preceding procedure when the product from Example V is replaced by 4.48 g. (0.01 mole) of the product from Example VI, prepared from pyromellitic dianhydride.

EXAMPLE XII: Preparation of Additional Polymers from Imide-Nitrile Diamines.

A solution of 4.48 g. (0.01 mole) of the product of Example VI, prepared from pyromellitic dianhydride, in 50 ml. of N,N-dimethylacetamide is stirred while adding 3.19 g. (0.01 mole) of 2,5-dicarbomethoxy terephthaloyl chloride. After stirring for an hour at 50° C., 5 g. of propylene oxide is added to neutralize hydrogen chloride. A polymer is obtained containing imide, nitrile, amide and ester groups. Curing at 300° C. gives a polymer containing imide and nitrile groups. Further cure at 400° C. gives a polymer containing imide linkages and isoindoloquinazolinedione ring systems.

This procedure is repeated, substituting 2.03 g. (0.01 mole) of isophthaloyl chloride for the 2,5-dicarbomethoxy terephthaloyl chloride. In this case the initial polymer contains amide, imide, and nitrile groups. The fully cured polymer contains amide linkages and isoindoloquinazolinedione ring systems.

The procedure is repeated, substituting 2.11 g. (0.01 mole) of trimellitoyl anhydride chloride for the 2,5-dicarbomethoxy terephthaloyl chloride. The initial polymer contains imide, amide acid, nitrile and amide linkages. Cure at 250°–300° C. for an hour gives a polymer containing imide, nitrile and amide groups. Further cure at 400° C. converts a portion of the imide and nitrile groups to isoindoloquinazolinedione ring systems.

The procedure is repeated, substituting 2.50 g. (0.01 mole) of 4,4'-diphenylmethanediisocyanate for the 2,5-dicarbomethoxy terephthaloyl chloride and eliminating the addition of propylene oxide. The polymer obtained contains imide, nitrile and urea linkages. Curing at temperatures above 300° C. gives a polymer containing other heterocyclic ring systems.

While I have shown and described certain presently preferred embodiments and uses of my invention, it is to be distinctly understood that the invention is not limited thereto but may be otherwise variously embodied and used.

I claim:
1. 2,4 diaminobenzonitrile.